US010975981B2

(12) United States Patent
St-Jean et al.

(10) Patent No.: US 10,975,981 B2
(45) Date of Patent: Apr. 13, 2021

(54) LIQUID DISPOSAL APPARATUS FOR TRANSFER CARTS

(71) Applicant: STERIS Inc., Temecula, CA (US)

(72) Inventors: Hugo St-Jean, Quebec (CA); Louis-Phillipe Gaudreau, Quebec (CA); Xavier Elie-Dit-Cosaque, Sainte-Brigitte-de-Laval (CA); Jaime Estevez, Quebec (CA); Luc Tremblay, Quebec (CA)

(73) Assignee: STERIS Inc., Temecula, CA (US)

( * ) Notice: Subject to any disclaimer, the term of this patent is extended or adjusted under 35 U.S.C. 154(b) by 0 days.

(21) Appl. No.: 16/385,071

(22) Filed: Apr. 16, 2019

(65) Prior Publication Data
US 2019/0346060 A1    Nov. 14, 2019

Related U.S. Application Data

(60) Provisional application No. 62/668,441, filed on May 8, 2018.

(51) Int. Cl.
*F16K 31/44* (2006.01)
*B08B 13/00* (2006.01)

(52) U.S. Cl.
CPC .............. *F16K 31/44* (2013.01); *B08B 13/00* (2013.01); *Y10T 137/5762* (2015.04)

(58) Field of Classification Search
CPC ... F16K 31/44; B08B 13/00; Y10T 137/5762; Y10T 137/5835
USPC ..................................... 137/312; 141/86-88
See application file for complete search history.

(56) References Cited

U.S. PATENT DOCUMENTS

| 2,157,112 A * | 5/1939 | Bonner .................. A47L 15/06 |
| | | 134/103.2 |
| 3,568,691 A | 3/1971 | Kennedy et al. |
| 3,863,985 A | 2/1975 | Zuber |
| 5,069,464 A | 12/1991 | Braconnier |
| 6,119,736 A * | 9/2000 | Huang et al. .......... B62B 3/006 |
| | | 141/86 |
| 6,203,036 B1 | 3/2001 | La Vaute et al. |
| 7,137,419 B1 * | 11/2006 | Reeves ................ B01D 29/085 |
| | | 141/340 |

(Continued)

OTHER PUBLICATIONS

International Preliminary Report on Patentability issued in International Application No. PCT/US2019/028053 dated Jul. 5, 2019. Year: 2019).*

(Continued)

*Primary Examiner* — Kevin L Lee
(74) *Attorney, Agent, or Firm* — Kusner & Jaffe (57) ABSTRACT

A fluid collection and disposal device for a transfer cart used for transporting wet articles is comprised of a tray disposed below articles to be transported on a transfer cart. The tray has a drain opening. A conduit extends from the drain opening to an exterior side of the transfer cart. A valve assembly is connected to the conduit for controlling fluid flow through the conduit. The valve assembly is comprised of a valve element moveable between a closed, first position restricting flow of fluid through the conduit and an opened, second position allowing flow of fluid through the conduit. An actuator is provided for moving the valve element from the closed position to the open position. The actuator is moveable by physical engagement with an external stop.

9 Claims, 6 Drawing Sheets

(56) References Cited

U.S. PATENT DOCUMENTS

| | | | |
|---|---|---|---|
| 7,422,038 B2 * | 9/2008 | Boler, Jr. ................ | A47L 13/51 |
| | | | 137/313 |
| 9,375,520 B2 | 6/2016 | Martini et al. | |
| 1,008,706 A1 | 10/2018 | Hall | |
| 2014/0339803 A1 | 11/2014 | Hammer | |

OTHER PUBLICATIONS

Website printout of "Ergo Handle Cart with Drain," Vestil Manufacturing, https://www.youtube.com/watch?v=8_9vhU7qqsM, accessed Aug. 1, 2012.

International Preliminary Report on Patentability with attached Written Opinion issued in International Application No. PCT/US2019/028053 dated Nov. 19, 2020.

* cited by examiner

LIQUID DISPOSAL APPARATUS FOR TRANSFER CARTS

RELATED APPLICATIONS

This application claims the benefit of U.S. Provisional Application No. 62/668,441, filed May 8, 2018, said provisional application is hereby fully incorporated herein by reference.

FIELD OF THE INVENTION

The present invention relates generally to a fluid collection and disposal system, and more particularly, to a fluid collection and disposal system for use on transfer carts that move medical instruments and equipment.

BACKGROUND OF THE INVENTION

Numerous types of articles, such as medical instruments, apparatus and devices, are used in hospitals and medical facilities for care of patients. Following such use, it is necessary to clean, i.e., wash and decontaminate such articles prior to subsequent use. The washer/decontamination unit is typically preformed in large washers/decontamination units located in medical service areas within the hospital medical facility. The articles to be cleaned are typically placed in large racks that are then placed within the washers/decontamination units. Following washing/decontamination of the articles, the racks containing the clean articles are typically moved by carts to "cool down areas" or "prep stations" where the articles are separated and packaged for subsequent use.

Articles removed from the washers/decontamination units are often wet and liquid drips from the cleaned articles. To avoid creating slipping hazards on the floors of these service areas, the transfer carts typically include pans or trays beneath the racks to collect liquid dripping from the racks or articles therein. The trays or pans may include a drain opening having a stopper or plug therein, wherein the pan or tray may be drained once it is filled with liquid by moving the transfer cart over a floor drain or fluid collection basin. A service technician can then physically remove the stopper or plug in the drain opening to allow the collected fluid to flow out.

It is also known to collect fluid from the trays in a receptacle or container (reservoir) located beneath the tray. These receptacles (reservoirs) are typically formed of translucent plastic materials which allow the service technician to monitor the amount of fluid collected therein. Once a container becomes full, the service technician removes the container (reservoir) from the cart and dumps its contents into a drain or collection basin.

As will be appreciated, both of the foregoing arrangements requires monitoring by the service technician of the fluid level in the tray or receptacle (reservoir) and participation of the service technician to remove physically a receptacle (reservoir) from the transfer cart or to remove a plug or stopper in a drain in a tray or pan to allow fluid to be removed from the transfer cart.

Further, recent developments in technology have contemplated the use of robots to physically move the transfer carts between washers and workstations which would eliminate human involvement in monitoring the collected fluid levels and dumping of the fluids.

The present invention provides a fluid collection and disposal system that does not require human monitoring and active participation in disposing of fluids collected in medical transfer carts.

SUMMARY OF THE INVENTION

In accordance with present invention, there is provided a fluid collection and disposal system for use on transfer carts that transfer medical equipment.

An advantage of the present invention is a fluid collection and disposal system for collecting and draining fluid from washed articles and racks transported by transfer carts in a medical facility.

Another advantage of the present invention is a fluid collection and disposal system as described above that is automatically actuated when a transfer cart is moved to a workstation or storage location.

A still further advantage of the present invention is a fluid collection and disposal system as described above that finds advantageous use on manually motivated transfer carts or robotic transfer carts.

A still further advantage of the present invention is a fluid collection and disposal system as described above wherein draining of the transfer cart does not require operator manipulation.

A still further advantage of the present invention is a fluid collection and disposal system as described above that does not require a storage container (reservoir) under the rack and does not require a large storage area for storing large volumes of collected fluid.

These and other advantages of the present invention will become apparent from the following description of the illustrated embodiments taken together with the accompanying drawings and the impending claims.

BRIEF DESCRIPTION OF THE DRAWINGS

The invention may take physical form in certain parts and arrangements of parts, a preferred embodiment of which will be described in detail in the specification and illustrated in the accompanying drawings, which form a part hereof, and wherein.

DETAILED DESCRIPTION OF THE INVENTION

Figure 1:
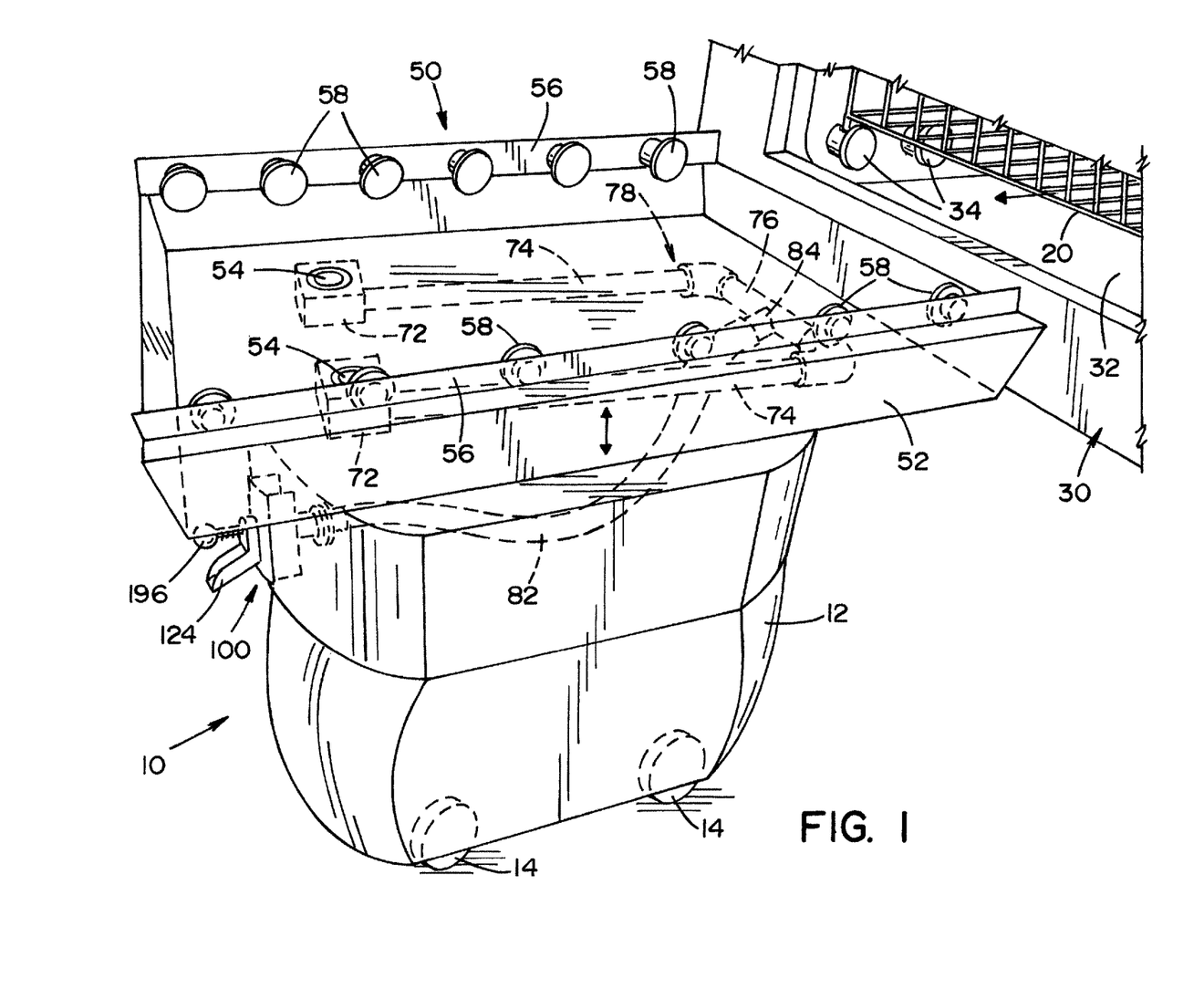
FIG. 1 is a top perspective view of a fluid collection and disposal device for a transfer cart that transports wet articles, illustrating a preferred embodiment of the present invention.

Referring now to the drawings for the purpose of illustrating the preferred embodiments of invention only and not for the purpose of limiting the same, FIG. 1 shows a cart 10 for transferring medical articles in a washing/decontamination service area. Cart 10 is operable to transfer a rack 20 (partially shown in FIG. 1) containing "articles" between a washer/decontamination unit 30 (partially shown in FIG. 1), a work station 40 (partially shown in FIG. 5) and a storage location (not shown) within the washing/decontamination service area. As used herein, the term "articles" refers to medical instruments such as, by way of example and not limitation, instruments used in surgical procedures, medical devices such as endoscopes, or medical appliances such as bed pans or glassware used in hospital or medical facilities. Cart 10 may be manually motivated, i.e., moved by a service technician, or may be a robotic device that moves automatically under preprogrammed controls. In the embodiment shown, a robotic cart 10 is illustrated. Cart 10 is comprised of housing 12 having casters or rollers 14 on the lower ends thereof. Rack 20 is dimensioned to be supported on cart 10 and to be moved thereby. Rack 20 is dimensioned to receive articles to be cleaned or decontaminated in a washing chamber 32 within washer/decontamination unit 30. Typically rollers 34 are provided within washing chamber 32 to allow the racks to be easily moved into and out of washer/decontamination unit 30, as is conventionally known.

In accordance with the present invention, a fluid collection and disposal device 50 is provided on top of cart 10. Fluid collection and disposal device 50 is comprised of a tray 52. In accordance with one aspect of the present invention, tray 52 is attached to cart 10 by means that allowing vertical movement of tray 52. In the embodiment shown, four (4) lifting devices 62 are disposed at the corners of tray 52 to facilitate vertical adjustment of tray 52 relative to cart 10. Lifting devices 62 may be pneumatic or hydraulic pistons, electric linear actuators are any other mechanical system to effect reciprocal vertical movement. Tray 52 is dimensioned to receive a rack 20 from washer/decontamination unit 30 and to collect liquid that may drip from articles within rack 20 following a washing/decontamination cycle. In this respect, tray 52 is rectangular in shape and has an outer profile larger than rack 20. Tray 52 includes spaced-apart, parallel, vertical side walls 56, each side wall 56 having a plurality of spaced-apart rollers 58. Rollers 58 are dimensioned and positioned on tray 52 to be alignable and in registry with rollers 34 in washing chamber 32 to allow a rack 20 to easily roll from washing chamber 32 onto cart 10, or vice versa, as shall be described in greater detail below.

Figure 2:
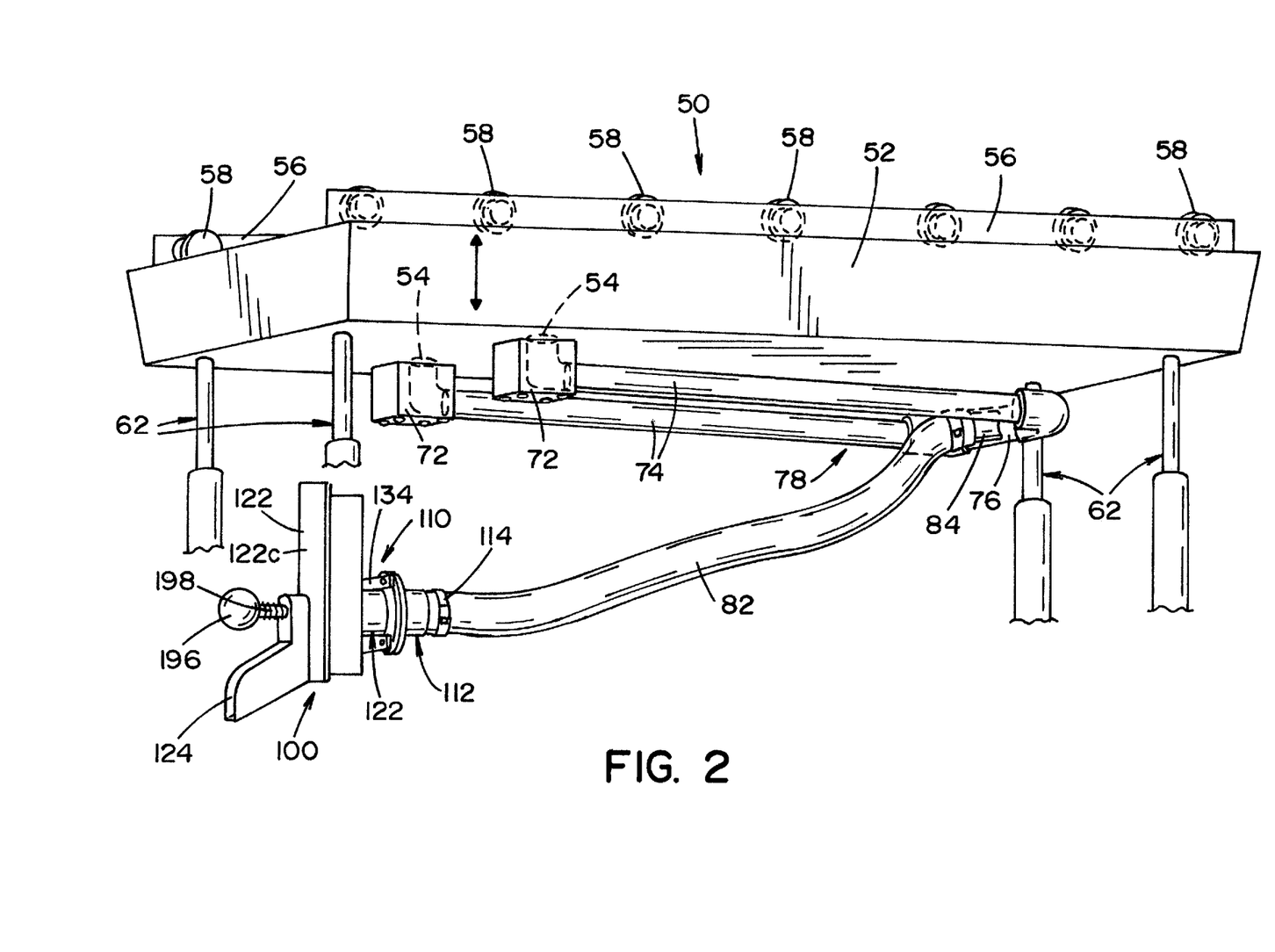
FIG. 2 is a bottom perspective view of the fluid collection and disposal device shown in FIG. 1.

Drain openings 54 are provided in the bottom of tray 52. In this respect, tray 52 is preferably formed to slope slightly toward drain openings 54 to facilitate draining of liquid therefrom, as shall be described in greater detail below. Drain openings 54 communicate with openings in blocks 72 beneath tray 52, as best seen in FIG. 2. Elongated pipe sections 74 extend from each block 72. The ends of pipe sections 74 are joined by a transverse pipe section 76. In the embodiment shown, pipe sections 74 and 76 form a generally U-shaped, closed pipe circuit 78.

A flexible conduit 82, disposed below tray 52, is fluidly connected to the pipe circuit 78. Conduit 82 is fluidly connected to transverse pipe section 76 by means of a T-fitting 84. In the embodiment shown, conduit 82 is formed of a flexible material such as, by way of example and not limitation, a flexible polymer material. Conduit 82 defines an inner fluid passage 82a that communicates with the internal openings defined by pipe circuit 78 and drain openings 54.

The other end of conduit 82 is connected to a fluid release assembly 100 that is disposed at one side of cart 10. Fluid release assembly 100 communicates with fluid passage defined by flexible conduit 82 and controls the flow of fluid through the fluid passage. Fluid release assembly 100 is comprised of a two-part housing 110 containing a valve assembly 150. Housing 110 is comprised of a conduit connection section 112 and a mounting section 122.

Conduit connection section 112 has a tubular body 112a and a tubular connector 112b extending from one end thereof. An outwardly extending, annular flange 112c is formed at a second end of tubular body 112. In the embodiment shown, body 112a and connector 112b are cylindrical in shape. Connector 112b has a barbed outer surface dimensioned to receive conduit 82. Conduit 82 is secured to connector 112b by a conventional hose clamp 114.

Mounting section 122 is comprised of tubular body 122a that includes an outwardly extending flange 122b at one end thereof. Flange 122b is dimensioned to engage and mate with the flange 112c on conduit connection section 112.

Figure 3:
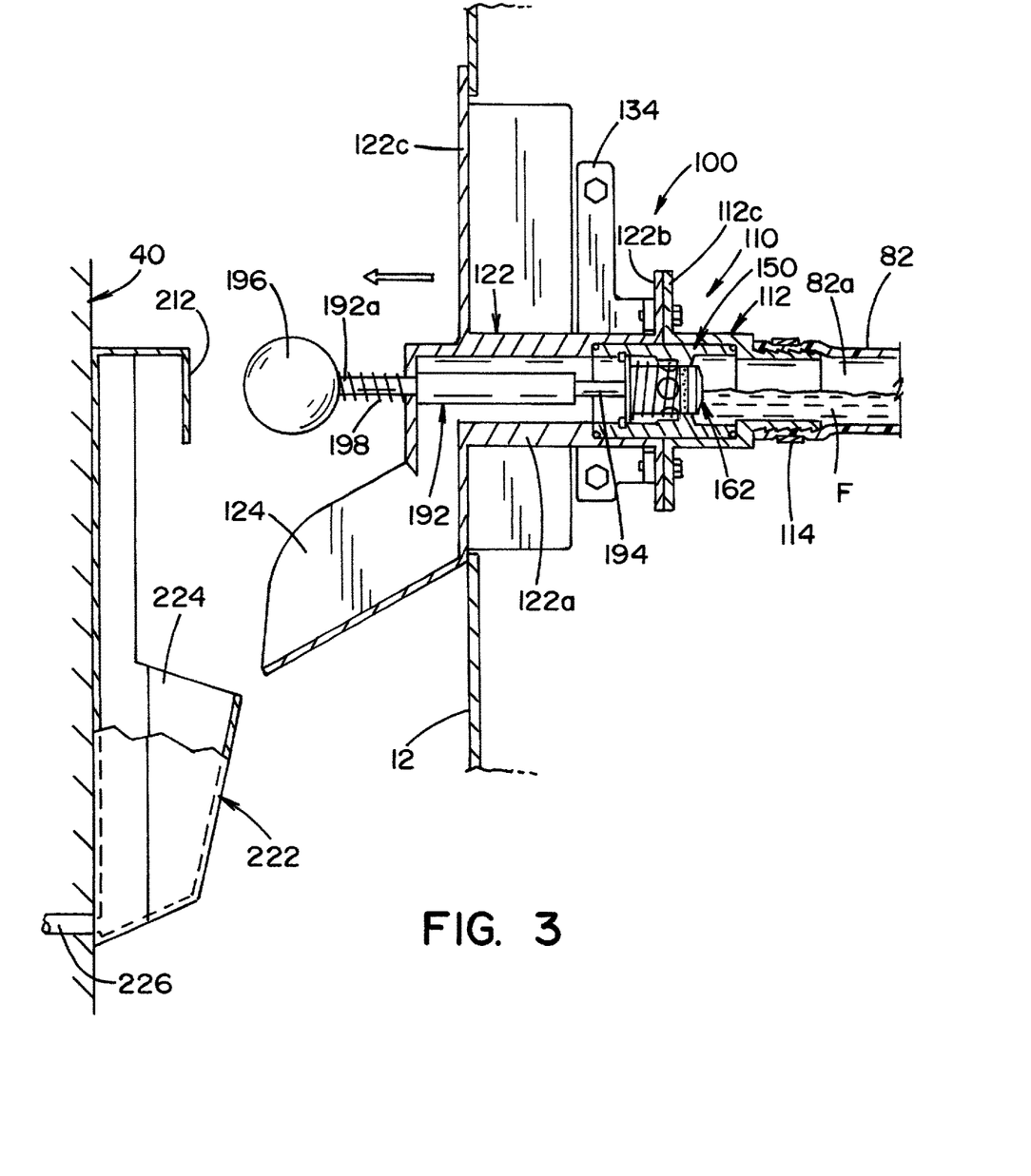
FIG. 3 is a side sectional view of a valve assembly for controlling flow of fluid from the fluid collection and disposal device.

A fascial panel 122c extends from a second end of tubular body 122a. Fascial panel 122c extends over an opening in housing 12 of cart 10, as best seen in FIG. 3. A downwardly angled spout 124 extends from fascial panel 122c and outwardly from cart 10. Spout 124 communicates with the passage defined tubular body 122a.

Conduit connection section 112 and mounting section 122 are dimensioned to be fastened together by conventional fasteners 132 extending through openings in flanges 112c, 122b into threaded openings in a bracket 134 that is mounted on cart 10. When attached together, conduit connector section 112 and mounting section 122 define an internal cylindrical recess 142, best seen in FIGS. 4 and 6.

A valve assembly 150 is disposed and captured within a cylindrical recess 142 that is defined between the conduit connection section 112 and mounting section 122.

Annular seals 144 are disposed between valve body 152 and conduit connection section 112 and mounting section 122 to form a fluid-tight seal therebetween. In the embodiment shown, seals 144 are O-rings disposed at the end of valve body 152.

Figure 4:
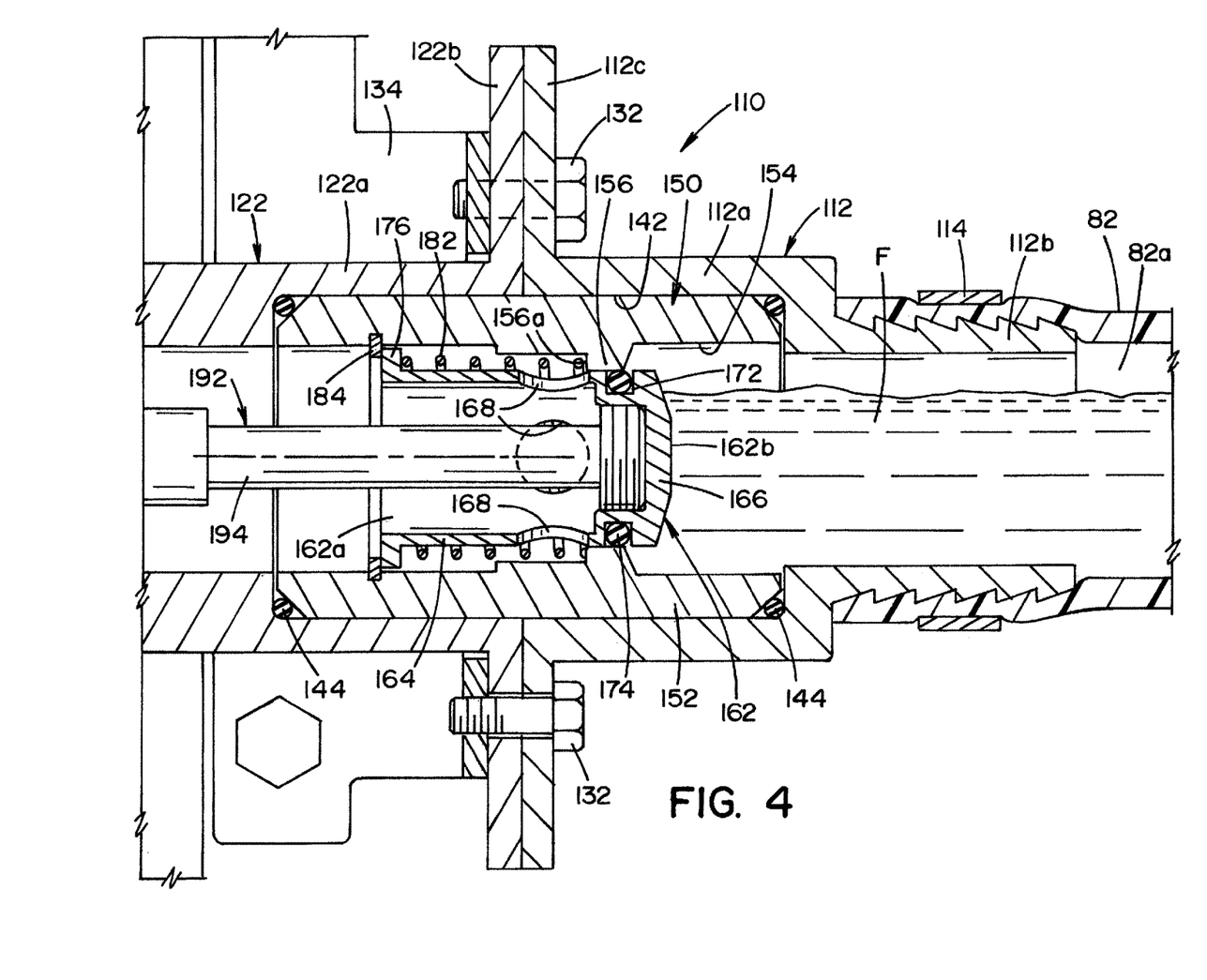
FIG. 4 is an enlarged view of the valve assembly shown in FIG. 3, showing a poppet valve in a closed position maintaining fluid within the fluid collection and disposal device.
Figure 6:
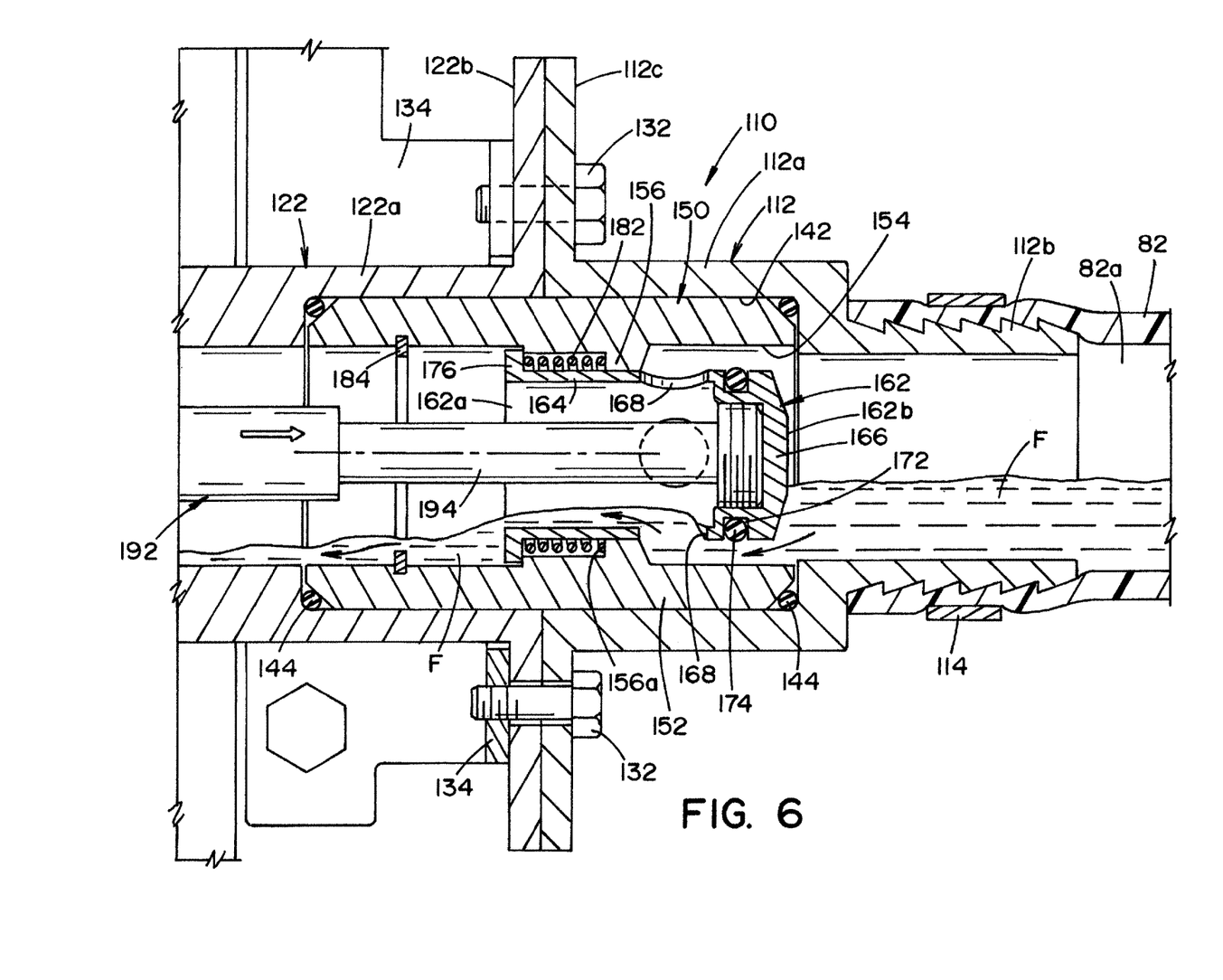
FIG. 6 is an enlarged view of the valve assembly shown in FIG. 5, showing the poppet valve in an open position allowing fluid to flow through the valve assembly.

Valve assembly 150 is comprised of a tubular valve body 152 defining an opening 154 therethrough. A poppet valve 162 is disposed within opening 154 in valve body 152. Poppet valve 162 is generally cup-shaped and has an opened end 162a and a closed end 162b. Poppet valve 162 has a tubular side wall 164 that defines a tubular body and an end wall 166 that defines closed end 162b. Openings 168 are formed in side wall 164 of poppet valve 162. In the embodiment shown, poppet valve 162 is cylindrical in shape and includes an annular groove 172 in the outer surface thereof. Annular groove 172 is disposed between openings 168 in side wall 164 and end wall 166 of poppet valve 162. O-ring 174 is disposed within annular groove 172 and is dimensioned to engage a valve seat 156 formed along the inner surface of valve body 152 (as best seen in FIGS. 4 and 6). An outwardly extending flange 176 is formed along opened end 162a of valve 162. A biasing element 182 biases poppet valve 162 to a normally closed, first position (best seen in FIG. 4) where O-ring 174 engages valve seat 156, thereby preventing fluid (designated "F" in the drawings) in conduit 82 from flowing past valve 162. In the embodiment shown, biasing element 182 is a spring that surrounds side wall 164 of poppet valve 162. Spring 182 is disposed between an annular surface 156a defined by valve seat 156 and outward extending flange 176 on valve 162. In the embodiment shown, a stop 184 is provided along the inner surface of valve body 152. Stop 184 is comprised of a lock ring received within an annular groove along the inner surface of valve body 152.

A valve actuator 192 is connected to poppet valve 162. Actuator 192 extends from valve assembly 150 and has a free end 192a that extends beyond the end of valve assembly 150 and beyond the outer periphery of cart 10.

Actuator 192 is an elongated rod 194 attached at one end to end wall 166 of poppet valve 162. In the embodiment shown, the end of actuator 192 is threaded to be received in a threaded bore in end wall 166. Actuator 192 extends through poppet valve 162 and through mounting section 122. A pad 196, in the form of a resilient ball, is attached to the free end of rod 194.

As best seen in FIG. 3, pad 196 is disposed above spout 124 (best seen in FIGS. 3 and 4). A biasing element 198, acting against mounting section 122, biases actuator rod 194 and poppet valve 162 toward the closed, first position. Rod 194 and poppet valve 162 are moveable from the closed, first position to an open, second position (best seen in FIGS. 5 and 6). In the open, second position, O-ring 174 on poppet valve 162 is moved away from valve seat 156, and openings 168 in poppet valve 162 communicate with the internal passage of conduit 82.

As discussed above, cart 10 is used to transfer a rack 20 from a washer/decontamination unit 30 and to a work station 40 or storage location (not shown). In this respect, cart 10 is designed to engage or "dock" with a washer/decontamination unit 30, work station 40 or a storage location. When docking with a washer/decontamination unit 30, a work station 40 or a storage location, cart 10 is positioned in a specific location relative to washer/decontamination unit 30, the work station 40 or the storage unit to allow a rack 20 on cart 10 to be transferred to and from cart 10 and to and from washer/decontamination unit 30, work station 40 or the storage location. In other words, cart 10 is dimensioned to interact or engage with the washer/decontamination unit 30, work station 40 or storage location at specific locations that shall hereinafter be referred to as "docking locations."

Figure 5:
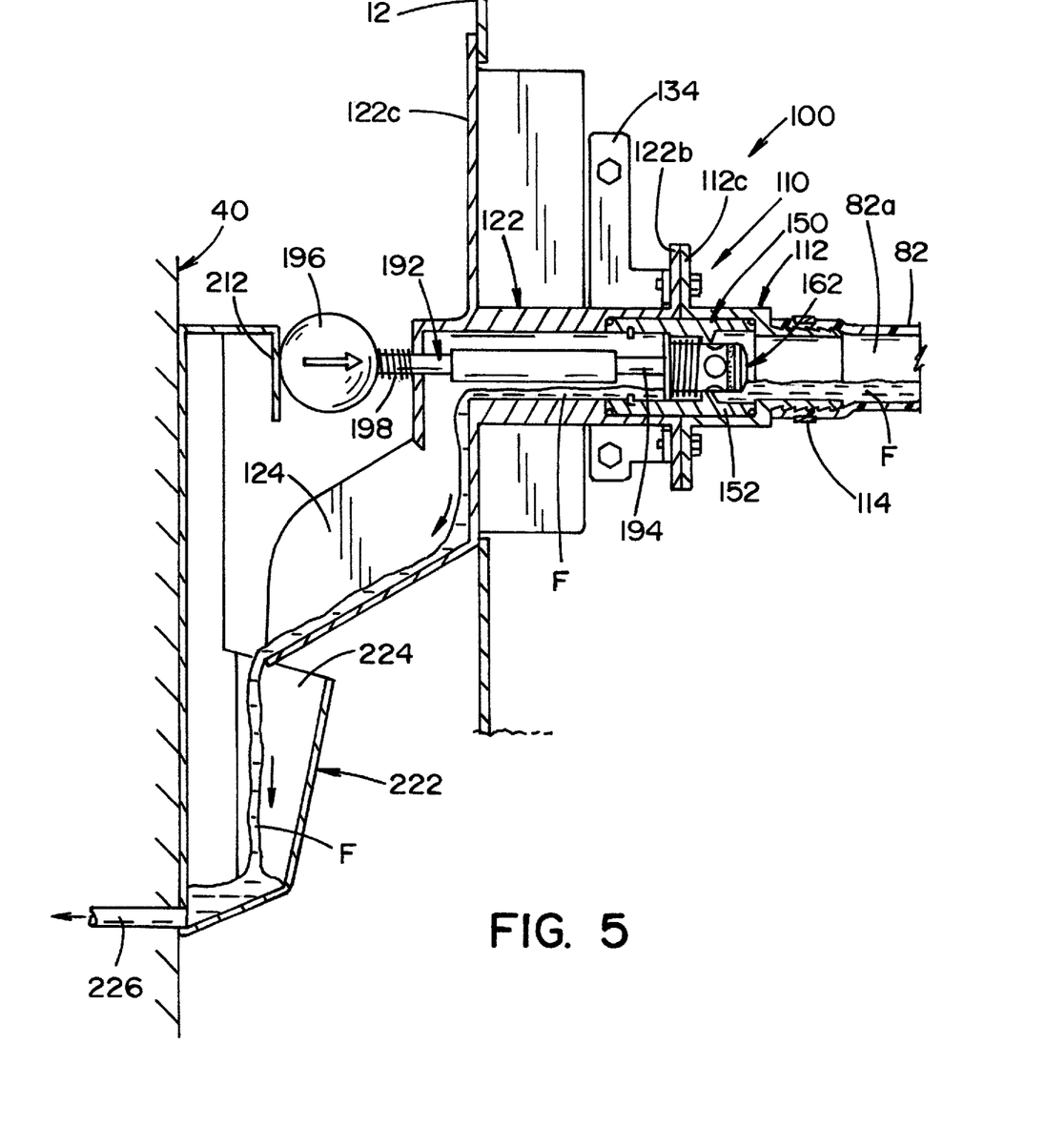
FIG. 5 is a side sectional view of the valve assembly shown in FIG. 3, showing the valve assembly engaging a stop at a work station and the valve assembly in an open position to allow fluid to drain from the fluid collection and disposal device to a receiving receptacle.

In accordance with another aspect of the present invention, a stop or barrier 212, best seen in FIGS. 3 and 5, is provided at a "docking location" to engage pad 196 on rod 194 of actuator 192. When cart 10 "docks" with a docking station, the pad 196 on the rod 194 engages stop 212 and causes poppet valve 162 to move from its normally closed, first position (as shown in FIGS. 3 and 4) to an opened, second position (as shown in FIGS. 5 and 6), as cart 10 moves toward a docked position at a docking location.

In accordance with another aspect of the present invention, the docking location also preferably includes a funnel-like housing 222 (best seen in FIGS. 3 and 5) having an opening 224 therein to receive spout 124 of mounting section 122. In the embodiment shown, a portion of housing 222 defines stop 212. A drain line 226 connects housing 222 to a drain or receptacle for collecting liquids "F" released from cart 10, as shall be described in greater detail below.

Referring now to the operation of the present invention, as indicated above, transfer cart 10 is used to transfer washed/decontaminated articles from a washer/decontamination unit 30 to a work station 40 or storage location where the washed/decontaminated articles are removed from a rack 20 and separated for further use or for storage until further use. As indicated above, it is not unusual for articles that have been washed/decontaminated to contain residual fluid "F" thereon, which fluids may then drip onto tray 52 on cart 10 that is located below rack 20. Fluid "F" is collected in tray 52 and flows toward drain opening 54 in tray 52 to conduit 82 therebeneath.

Preferably, there is no stop 212 or barrier on washer/decontamination unit 30 that would cause valve actuator rod 194 to move poppet valve 162 from its normally closed, first position to an opened, second position. In this respect, the exterior configuration of washer/decontamination unit 30 is dimensioned to where poppet valve 162 remains in its normally closed, first position. In this configuration, any fluids "F" that would drip from rack 20 onto tray 52 while in position relative to washer/decontamination unit 30 or during transport from washer/decontamination unit 30 to a work station 40 or storage location would collect within conduit 82 beneath tray 52. As will be appreciated, depending on the allowable space beneath tray 52, conduit 82 can be dimensioned to collect different amounts of fluid "F" depending upon the dimensions of conduit 82.

As noted above, the washed/decontaminated articles are preferably moved to a work station 40 for removal of the washed/decontaminated articles from rack 20. Preferably, a drain or fluid collection container is provided at the docking location with work station 40 or storage location. Work station 40 or storage location preferably includes funnel-like housing 222 and stop 212 as described above. In this respect, as cart 10 approaches work station 40, pad 196 on rod 194 engages stop or barrier 212 on funnel-like housing 222, thereby causing poppet valve 162 to move from its normally closed, first position to an opened, second position as spout 124 enters opening 224 of funnel-like housing 222. As will be appreciated, opening poppet valve 162 allows any fluid "F" collected within conduit 82 or tray 52 to flow through valve assembly 150 to spout 124 and into funnel-like housing 222. From here, fluid 'F" is drained, preferably to a collection tank or to a floor drain, to dispose of the collected fluid "F".

Whenever cart 10 is removed from work station 40 or storage location, poppet valve 162 returns to a closed, first position, thereby collecting any subsequent fluid "F" that may drip onto tray 52 and thereby storing the fluid "F" in conduit 82 until cart 10 engages another docking station having the valve actuating system associated therewith.

The present invention thus provides an automatic method of draining fluid "F" from a cart 10 used to transfer medical devices from a washer/decontamination unit 30 to a work station 40 or storage location. Because cart 10 always docks in the same location with a work station 40 or storage location to facilitate transferring a rack 20 from cart 10, the present system enables automatic draining of any collected fluid "F" without manual intervention by the service technician moving cart 10. It further does not require monitoring any collected fluid "F" since fluid "F" is automatically dumped each time cart 10 is moved to work station 40 or storage location, i.e., to a docking position.

Still further, flexible conduit 82 allows advantageous application with robotic systems or systems that may have a rack height-adjustment feature for adjusting the height of rack 20 to facilitate removal washer/decontamination unit 30 having different opening heights. In other words, rack 20 may have a height-elevation-adjusting feature, and flexible hose 82 allows for adjustments in the heights of tray 52 for receiving a rack 20.

The foregoing description relates to a specific embodiment of the invention. It should be appreciated that this embodiment is described for the purpose of illustration only, and that numerous alterations and modifications may be practiced by those skilled in the art without departing from the spirit and the scope of the invention. For example, the present invention has been described with respect to a spout on the mounting structure that is located reasonably close to the valve release stem, wherein the spout interacts with a funnel-like housing at a docking location to release fluids into the funnel-like housing. As will be appreciated, the mounting structure on the cart could be adapted to include a conduit for conducting the fluid down near a floor level, wherein fluid from the tray collected by the present invention could be released directly into a floor drain at a docking location. It is intended that all such modifications and alterations be included insofar as they come within the scope of the invention as claimed or the equivalence thereof.

Having described the invention, the following is claimed:

1. A fluid collection and disposal device for a transfer cart used for transporting wet articles, said device comprising:
    a tray disposed below articles to be transported on the transfer cart, said tray having a bottom in which a drain opening is defined, said drain opening being configured to allow fluid to flow therethrough;
    a conduit extending from said drain opening to an exterior side of said transfer cart;
    a valve assembly connected to said conduit for controlling said flow of said fluid through said conduit, said valve assembly comprised of:
        a valve element moveable between a closed, first position restricting said flow of said fluid through said conduit and an opened, second position allowing said flow of said fluid through said conduit, and
        an actuator for moving said valve element from said closed position to said opened position, said actuator being moveable by physical engagement with an external stop; and
    vertical lifting means configured to support the tray on the transfer cart and facilitate vertical adjustment of the tray relative to the transfer cart.

2. A fluid collection and disposal device as claimed in claim 1, wherein said external stop is located at a working station for said transfer cart, and
    wherein said actuator on said cart is dimensioned to engage said external stop and cause said valve element to move to said opened position.

3. A fluid collection and disposal device as claimed in claim 1, wherein said conduit is flexible.

4. A fluid collection and disposal device as claimed in claim 3, wherein said conduit is a polymer hose connected to said tray.

5. A fluid collection and disposal device as claimed in claim 1, further comprising a spout at a free end of said conduit for directing said flow of said fluid from said conduit.

6. A fluid and collection disposal device as claimed in claim 5, wherein said working station includes a receptacle for receiving said spout, said receptacle having a funnel shape.

7. A fluid and collection disposal device as claimed in claim 6, wherein said receptacle is connected to a drain.

8. A fluid and collection disposal device as claimed in claim 1, wherein the tray slopes toward the drain opening to facilitate draining of the fluid into the drain opening.

9. A fluid collection and disposal device for a transfer cart used for transporting wet articles, said device comprising:
    a tray disposed below articles to be transported on the transfer cart, said tray having a bottom in which a drain opening is defined, said drain opening being configured to allow fluid to flow therethrough;
    a conduit extending from said drain opening to an exterior side of said transfer cart;
    a valve assembly connected to said conduit for controlling said flow of said fluid through said conduit, said valve assembly comprised of:
        a valve element moveable between a closed, first position restricting said flow of said fluid through said conduit and an opened, second position allowing said flow of said fluid through said conduit, and
        an actuator for moving said valve element from said closed position to said opened position, said actuator being moveable by physical engagement with an external stop; and
    a pipe circuit positioned between the drain opening and the conduit, the pipe circuit being fluidly communicable with the drain opening and the conduit.

* * * * *